United States Patent

Baker et al.

[11] Patent Number: 5,985,896
[45] Date of Patent: Nov. 16, 1999

[54] PIPERIDINE AND MORPHOLINE DERIVATIVES AND THEIR USE AS THERAPEUTIC AGENTS

[75] Inventors: Raymond Baker, Uley; Jason Matthew Elliott, Knockholt; Graeme Irvine Stevenson, Saffron Walden; Christopher John Swain, Duxford, all of United Kingdom

[73] Assignee: Merck Sharp & Dohme Ltd., Hoddesdon, United Kingdom

[21] Appl. No.: 08/981,526

[22] PCT Filed: Jun. 20, 1996

[86] PCT No.: PCT/GB96/01477

§ 371 Date: Dec. 18, 1997

§ 102(e) Date: Dec. 18, 1997

[87] PCT Pub. No.: WO97/01554

PCT Pub. Date: Jan. 16, 1997

[30] Foreign Application Priority Data

Jun. 28, 1995 [GB] United Kingdom ............ 9513121

[51] Int. Cl.⁶ .................. A61K 31/445; C07D 405/14
[52] U.S. Cl. .............................. 514/320; 546/196
[58] Field of Search .................. 546/196; 514/320

[56] References Cited

U.S. PATENT DOCUMENTS

| 5,232,929 | 8/1993 | Desai et al. ............... 514/314 |
| 5,661,162 | 8/1997 | MacLeod et al. ........... 514/331 |
| 5,719,147 | 2/1998 | Dorn et al. ............... 514/227.5 |

FOREIGN PATENT DOCUMENTS

| 0 577 394 | 1/1994 | European Pat. Off. . |
| WO 94/19323 | 9/1994 | WIPO . |
| WO 95/06645 | 3/1995 | WIPO . |

OTHER PUBLICATIONS

Burger "A guide to the chemical basis of drug design" Wiley–Interscience, p. 15, 1983.
Amour et al. "Tetrazole NK1 receptor antagonists . . . " Bioorg. Med. Chem. v.6, No. 9, pp. 1015–1020, 1996.

Primary Examiner—Ceila Chang
Attorney, Agent, or Firm—J. Eric Thies; David L. Rose

[57] ABSTRACT

The present invention provides compounds of formula (I), wherein $R^1$ is phenyl or a 5- or 6-membered aromatic heterocyclic group containing 1, 2, 3 or 4 heteroatoms, selected from nitrogen, oxygen and sulphur, which aryl or heteroaryl group is optionally substituted; $R^2$ is hydrogen, halogen, $C_{1-6}$alkyl, $C_{1-6}$alkoxy, $CF_3$, $OCF_3$, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl; $R^4$, $R^5$, $R^6$, $R^{9a}$ and $R^{9b}$, A, X, and Y are as defined in the specification; the dotted line is an optional double bond; $Q^1$ is oxygen, sulphur or —NH—; $Q^2$ is —N=, —NH—, —CH= or —CH₂—; and m is zero or 1; and pharmaceutically acceptable salts and prodrugs thereof. The compounds are of particular use in the treatment or prevention of pain, inflammation, migraine, emesis and postherpetic neuralgia.

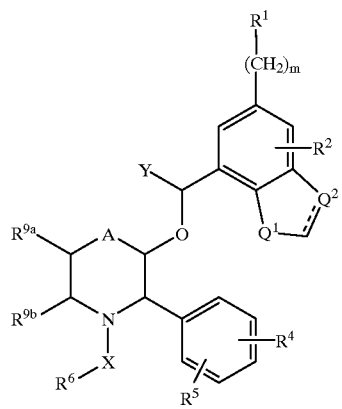

17 Claims, No Drawings

PIPERIDINE AND MORPHOLINE DERIVATIVES AND THEIR USE AS THERAPEUTIC AGENTS

This application is a 371 of PCT/GB96/01477 filed Jun. 20, 1996.

This invention relates to a class of aromatic compounds which are useful as tachykinin antagonists. More particularly, the compounds of the invention contain an amnine-substituted azo-heterocyclic moiety.

The tachykinins are a group of naturally occurring peptides found widely distributed throughout mammalian tissues, both within the central nervous system and in peripheral nervous and circulatory systems.

At present, there are three known mammalian tachykinins referred to as substance P, neurokinin A (NKA, substance K, neuromedin L) and neurokinin B (NKB, neuromedin K) (for review see J. E. Maggio, *Peptides* (1985) 6(suppl. 3), 237–242). The current nomenclature designates the three tachykinin receptors mediating the biological actions of substance P, NKA and NKB as the $NK_1$, $NK_2$ and $N_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A Giachetti, *J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 *Substance P in the Nervous System*, Ciba Foundation Symposium 91, 13–34 (published by Pitman) and Otsuka and Yanagisawa, "Does Substance P Act as a Pain Transmitter?" TIPS (1987) 8, 506–510], specifically in the transmission of pain in migraine (B. E. B. Sandberg et al, *J. Med Chem*, (1982) 25, 1009) and in arthritis [Levine et al *Science* (1984) 226, 547–549]. Tachykinins have also been implicated in gastrointestinal (GI) disorders and diseases of the GI tract such as inflammatory bowel disease [Mantyh et al *Neuroscience* (1988) 25(3), 817–37 and D. Regoli in "*Trends in Cluster Headache*" Ed. Sicuteri et al Elsevier Scientific Publishers, Amsterdam (1987) page 85)] and emesis [F. D. Tattersall et al, *Eur. J. Pharmacol.*, (1993) 250, R5-R6]. It is also hypothesised that there is a neurogenic mechanism for arthritis in which substance P may play a role [Kidd et al "A Neurogenic Mechanism for Symmetrical Arthritis" in *The Lancet*, Nov. 11, 1989 and Grbnblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et at, *Can. J. Pharmacol.* *Physiol.* (1988) 66, 1361–7], immunoregulation [Lotz et al, *Science* (1988) 241, 1218–21 and Kimball et al, *J. Immunol.* (1988) 141(10), 3564–9] vasodilation, bronchospasm, reflex or neuronal control of the viscera [Mantyh et al, *PNAS* (1988) 85, 3235–9] and, possibly by arresting or slowing β-amyloid-mediated neurodegenerative changes [Yankner et al, *Science* (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554–7].

Substance P may also play a role in demyelinating diseases such as multiple sclerosis and amyotrophic lateral sclerosis [J. Luber-Narod et al, poster *C.I.N.P. XVIIth Congress*, Jun. 28th–Jul. 2nd 1992], and in disorders of bladder function such as bladder detrusor hyper-reflexia (Lancet, May 16th 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

European patent specification no. 0 577 394 (published Jan. 5, 1994) discloses morpholine and thiomorpholine tachykinin receptor antagonists of the general formula

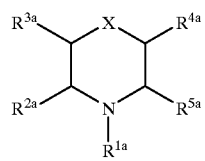

wherein $R^{1a}$ is a large variety of substituents;
$R^{2a}$ and $R^{3a}$ are inter alia hydrogen;
$R^{4a}$ is inter alia

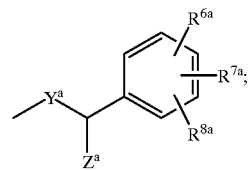

$R^{5a}$ is inter alia optionally substituted phenyl;
$R^{6a}$, $R^{7a}$ and $R^{8a}$ are a variety of substituents;
$X^a$ is O, S, SO or $SO_2$;
$Y^a$ is inter alia O; and
$Z^a$ is hydrogen or $C_{1-4}$alkyl.

International Patent Specification no. WO 95/06645 discloses piperidine derivatives as tachykinin receptor antagonists of the general formula

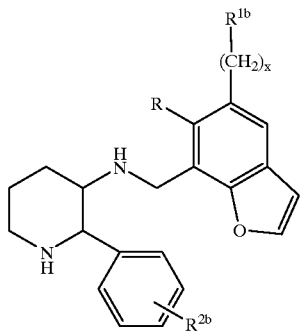

wherein R is hydrogen or $C_{1-4}$alkoxy;
$R^{1b}$ is phenyl, optionally substituted by —(CH$_2$)$_{1-2}$CONR$^{3b}$R$^{4b}$ or S(O)$_{1-2}$R$^{3b}$ or a 5-or 6-membered aromatic heterocycle containing 1, 2, 3 or 4 heteroatoms selected from O, N, or S, optionally substituted by $C_{1-4}$alkyl, CF$_3$, CN or —(CH$_2$)$_{1-2}$CONR$^{3b}$R$^{4b}$;
$R^{2b}$ is hydrogen or halogen;
$R^{3b}$ and $R^{4b}$ are hydrogen or $C_{1-4}$alkyl; and
x is zero or 1.

We have now found a further class of non-peptides which are potent antagonists of tachykinins, especially of substance P.

The present invention provides compounds of the formula (I):

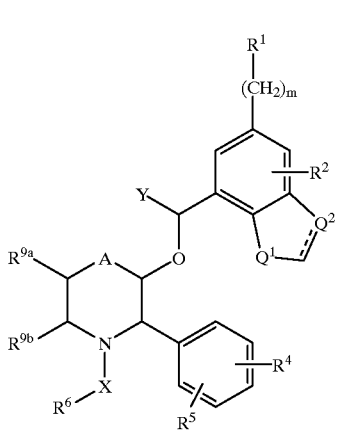

wherein
$R^1$ is phenyl or a 5- or 6-membered aromatic heterocyclic group containing 1, 2, 3 or 4 heteroatoms, selected from nitrogen, oxygen and sulphur, which aryl or heteroaryl group is optionally substituted by one or two substituents selected from halogen, $C_{1-6}$alkyl, $C_{1-6}$alkoxy, CF$_3$, OCF$_3$, NO$_2$, CN, SR$^a$, SOR$^a$, SO$_2$R$^a$, COR$^a$, CO$_2$R$^a$, (CH$_2$)$_n$CONR$^a$R$^b$, (CH$_2$)$_n$NR$^a$R$^b$ or (CH$_2$)$_n$NR$^a$COR$^b$, where R$^a$ and R$^b$ are independently hydrogen or $C_{1-4}$alkyl and n is zero, 1 or 2;
$R^2$ is hydrogen, halogen, $C_{1-6}$alkyl, $C_{1-6}$alkoxy, CF$_3$, OCF$_3$, NO$_2$, CN, SR$^a$, SOR$^a$, SO$_2$R$^a$, CO$_2$R$^a$, CONR$^a$R$^b$, $C_{2-6}$alkenyl, $C_{2-6}$alkynyl or $C_{1-4}$alkyl substituted by $C_{1-4}$alkoxy, where R$^a$ and R$^b$ each independently represent hydrogen or $C_{1-4}$alkyl;
$R^4$ is hydrogen, halogen, $C_{1-6}$alkyl, $C_{1-6}$alkoxy, CF$_3$, NO$_2$, CN, SR$^a$, SOR$^a$, SO$_2$R$^a$, CO$_2$R$^a$, CONR$^a$R$^b$, $C_{2-6}$alkenyl, $C_{2-6}$alkynyl or $C_{1-4}$alkyl substituted by $C_{1-4}$alkoxy, where R$^a$ and R$^b$ each independently represent hydrogen or $C_{1-4}$alkyl;
$R^5$ is hydrogen, halogen, $C_{1-6}$alkyl, $C_{1-6}$alkoxy substituted by $C_{1-4}$alkoxy or CF$_3$;
$R^6$ is a 5-membered or 6-membered heterocyclic ring containing 2 or 3 nitrogen atoms optionally substituted by =O, =S or a $C_{1-4}$alkyl group, and optionally substituted by a group of the formula ZNR$^7$R$^8$ where
Z is $C_{1-6}$alkylene or $C_{3-6}$cycloalkylene;
$R^7$ is hydrogen, $C_{1-4}$alkyl, $C_{3-7}$cycloalkyl or $C_{3-7}$cycloalkylC$_{1-4}$alkyl, or $C_{2-4}$alkyl substituted by $C_{1-4}$alkoxy or hydroxyl;
$R^8$ is hydrogen, $C_{1-4}$alkyl, $C_{3-7}$cycloalkyl or $C_{3-7}$cycloalkylC$_{1-4}$alkyl, or $C_{2-4}$alkyl substituted by one or two substituents selected from $C_{1-4}$alkoxy, hydroxyl or a 4, 5 or 6 membered heteroaliphatic ring containing one or two heteroatoms selected from N, O and S;
or R$^7$, R$^8$ and the nitrogen atom to which they are attached form a heteroaliphatic ring of 4 to 7 ring atoms, optionally substituted by one or two groups selected from hydroxy or $C_{1-4}$alkyl optionally substituted by a $C_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is $C_{1-4}$alkyl optionally substituted by hydroxy or $C_{1-4}$alkoxy;
or R$^7$, R$^8$ and the nitrogen atom to which they are attached form a non-aromatic azabicyclic ring system of 6 to 12 ring atoms;
or Z, R$^7$ and the nitrogen atom to which they are attached form a heteroaliphatic ring of 4 to 7 ring atoms which may optionally contain an oxygen ring atom;
$R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;
the dotted line is an optional double bond;
A is —O— or —CH$_2$—;
$Q^1$ is oxygen, sulphur or —NH—;
$Q^2$ is —N=, —NH—, —CH= or —CH$_2$—;
X is an alkylene chain of 1 to 4 carbon atoms optionally substituted by oxo;
Y is hydrogen or a $C_{1-4}$alkyl group optionally substituted by a hydroxyl group; and
m is zero or 1; and pharmaceutically acceptable salts and prodrugs thereof According to an alternative aspect of the present invention, Y is a $C_{1-4}$alkyl group optionally substituted by a hydroxyl group.

Certain particularly apt compounds of the present invention include those wherein $R^1$ is a group selected from phenyl, pyrrole, furan, thiene, pyridine, pyrazole, imidazole, oxazole, isoxazole, thiazole, isothiazole, pyrazine, pyrimidine, pyridazine, triazole, oxadiazole, thiadiazole, triazine, and tetrazole, each of which aryl or heteroaryl groups being optionally substituted as previously defined.

Preferred compounds of the present invention are those wherein $R^1$ is a group selected from phenyl, furan, pyridine, pyrazole, imidazole, oxazole, isoxazole, pyrazine, pyrimidine, thiazole, 1,2,3-triazole, 1,2,4-triazole, 1,2,4-oxadiazole, 1,3,4-oxadiazole and tetrazole, each of which aryl or heteroaryl groups being optionally substituted as previously defined.

Particularly preferred compounds of the present invention are those wherein $R^1$ is a group selected from phenyl, furan, pyridine, pyrimidine, 1,2,3-triazole, 1,2,4-triazole and tetrazole.

An especially preferred class of compound of formula (I) is that wherein $R^1$ is the group

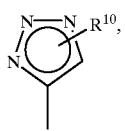

where $R^{10}$ is halogen, $C_{1-6}$alkyl, $C_{1-6}$alkoxy, $CF_3$, $OCF_3$, $NO_2$, CN, $SR^a$, $SOR^a$, $SO_2R^a$, $COR^a$, $CO_2R^a$, $(CH_2)_nCONR^aR^b$, $(CH_2)_nNR^aR^b$ or $(CH_2)_nNR^aCOR^b$, where $R^a$ and $R^b$ are hydrogen or $C_{1-4}$alkyl, and n is zero, 1 or 2.

Another especially preferred class of compound of formula (I) is that wherein $R^1$ is the group

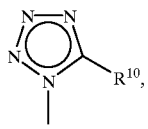

wherein $R^{10}$ is as previously defined.

$R^{10}$ is preferably hydrogen, $C_{1-4}$alkyl, especially methyl, $CF_3$, $(CH_2)_nCONR^aR^b$, $SOR^a$ or $SO_2R^a$ where $R^a$, $R^b$ and n are as previously defined.

Most aptly $R^2$ is hydrogen, $C_{1-4}$alkyl, $C_{1-4}$alkoxy, halogen, $CF_3$ or $OCF_3$.

Preferably $R^2$ is hydrogen or methoxy, especially hydrogen.

The group $R^2$ may be attached to any available position on the 6/5-fused ring. Most preferably $R^2$ is attached to the carbon atom in between the group $R^1$—$(CH_2)_m$— and the remainder of the molecule.

Most aptly $R^4$ is hydrogen.

Most aptly $R^5$ is hydrogen, fluorine, chlorine or $CF_3$.

Preferably $R^4$ is hydrogen and $R^5$ is hydrogen or 4-fluoro.

Most aptly $R^{9a}$ and $R^{9b}$ are each independently hydrogen or methyl.

Preferably $R^{9a}$ is hydrogen. Preferably $R^{9b}$ is hydrogen. Most preferably $R^{9a}$ and $R^{9b}$ are both hydrogen.

Preferably m is zero.

Preferably A is —O—.

Preferably $Q^1$ is an oxygen atom.

Preferably $Q^2$ is —CH= or —CH$_2$—.

Preferably the dotted line represents a double bond.

Regarding the definition of $R^1$ above, where $R^1$ represents 5- or 6-membered aromatic heterocyclic group, such a group may be attached to the remainder of the molecule via any available carbon or nitrogen atom.

The aryl or heteroaryl group represented by $R^1$ may be substituted by one or two substituents at any available position on the aryl or heteroaryl group.

When $R^1$ is a phenyl group, a suitable susbtituent is $SO_2CH_3$.

When $R^1$ is an aromatic heterocyclic group, preferred substituents include methyl, CN, $CF_3$ or $CON(CH_3)_2$. For instance, when $R^1$ is a pyridine group, suitable substituents include methyl, CN and $CON(CH_3)_2$; when $R^1$ is a pyrazole, imidazole, isoxazole or triazole group, suitable substituents include one or two methyl groups; and when $R^1$ is tetrazole, suitable substituents include methyl or $CF_3$.

From the foregoing it will be appreciated that a particularly apt sub-group of compounds of this invention are those of the formula (Ia) and pharmaceutically acceptable salts and prodrugs thereof:

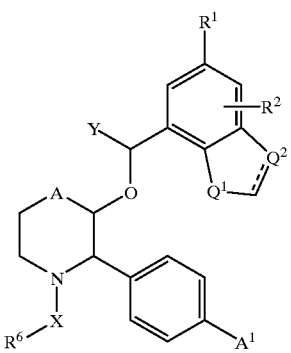

(Ia)

wherein

A, X, Y, $R^1$, $R^2$, $R^6$, $Q^1$, $Q^2$ and the dotted line are as defined in relation to formula (I) and $A^1$ is fluorine or hydrogen.

According to a second or further aspect of the present invention, a preferred class of compound of formula (I) or (Ia) is that wherein Y represents a $C_{1-4}$alkyl group; or a pharmaceutically acceptable salt or prodrug thereof.

According to a further or alternative aspect of the present invention, another preferred class of compound of formula (I) or (Ia) is that wherein $R^6$ is substituted at least by a group of the formula $ZNR^7R^8$ as defined above; or a pharmaceutically acceptable salt or prodrug thereof When the group Y in compounds of the formulae (I) or (Ia) is a $C_{1-4}$alkyl group susbtituted by a hydroxy group, a preferred group is the $CH_2OH$ group.

Another preferred group Y for compounds of the formulae (I) or (Ia) is the $CH_3$ group.

Particularly apt values for X for compounds of the formulae (I) or (Ia) include $CH_2$, $CH(CH_3)$ and $CH_2CH_2$ of which the $CH_2$ group is preferred.

Favourably $R^6$ is a 5-membered ring.

In particular, $R^6$ may, represent a heterocyclic ring selected from:

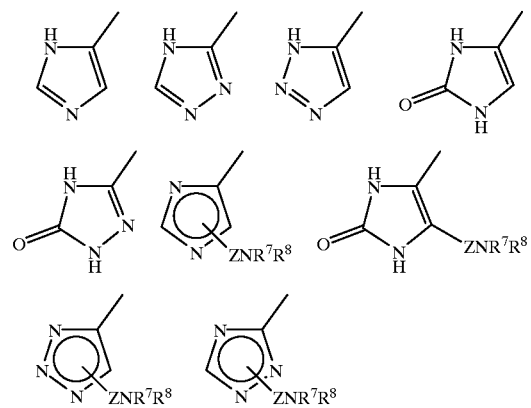

Particularly preferred heterocyclic rings represented by $R^6$ are selected from:

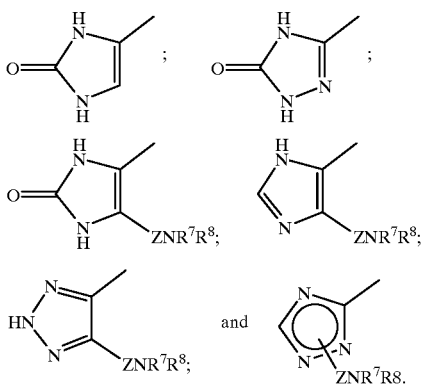

Most especially, $R^6$ may represent a heterocyclic ring selected from:

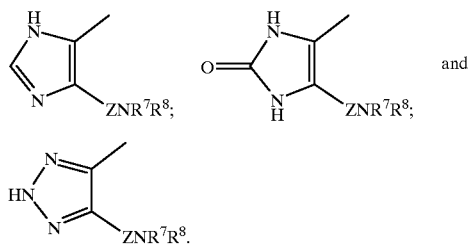

A particularly preferred heterocyclic ring represented by $R^6$ is:

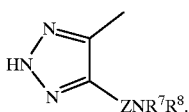

One favored group of compounds of this invention are of the formula (Ib) and pharmaceutically acceptable salts thereof.

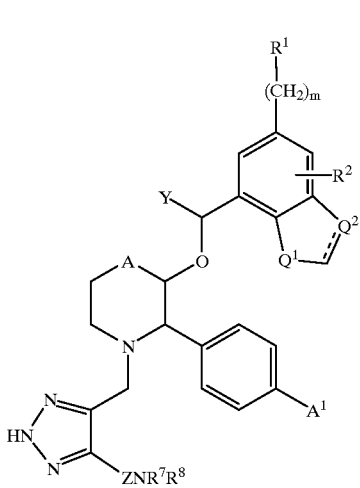

wherein $A^1$ is as defined in relation to formula (Ia), wherein A, Z, $R^1$, $R^2$, $R^7$, $R^8$, $Q^1$, $Q^2$, the dotted line and m are as defined in relation to formula (I) and wherein $Y^1$ is hydrogen or methyl.

A further favored group of compounds of the present invention are of the formula (Ic) and pharmaceutically acceptable salts thereof:

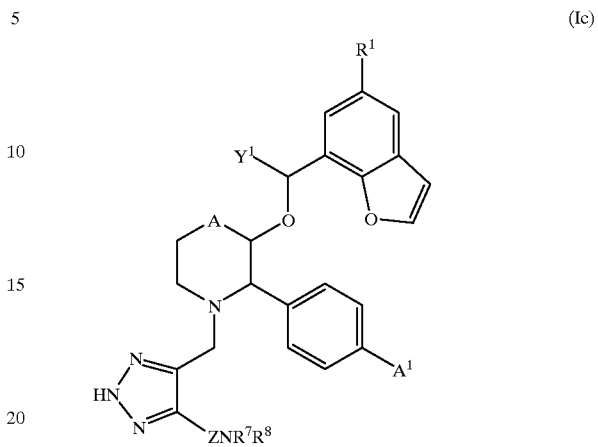

wherein $A^1$ is as defined in relation to formula (Ia); $Y^1$ is hydrogen or methyl; and $R^1$, $R^7$, $R^8$ and Z are as defined in relation to formula (I).

With respect to compounds of the formulae (I), (Ia), (Ib), and (Ic), Z may be a linear, branched or cyclic group. Favorably Z contains 1 to 4 carbon atoms and most favorably 1 or 2 carbon atoms. A particularly favorable group Z is $CH_2$.

With respect to compounds of the formulae (I), (Ia), (Ib), and (Ic), $R^7$ may aptly be a $C_{1-4}$alkyl group or a $C_{2-4}$alkyl group substituted by a hydroxyl or $C_{1-2}$alkoxy group, $R^8$ may aptly be a $C_{1-4}$alkyl group or a $C_{1-4}$alkyl group substituted by a hydroxyl or $C_{1-2}$alkoxy group, or $R^7$ and $R^8$ may be linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

Where the group $NR^7R^8$ represents a heteroaliphatic ring of 4 to 7 ring atoms and said ring contains a double bond, a particularly preferred group is 3-pyrroline.

Where the group $NR^7R^8$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.2.2]cdecyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^8$ represents a $C_{2-4}$alkyl group substituted by a 5 or 6 membered heteroaliphatic ring containing one or two heteroatoms selected from N, O and S, suitable rings include pyrrolidino, piperidino, piperazino, morpholino, or thiomorpholino. Particularly preferred are nitrogen containing heteroaliphatic rings, especially pyrrolidino and morpholino rings.

Particularly suitable moieties $ZNR^7R^8$ include those wherein Z is $CH_2$ or $CH_2CH_2$ and $NR^7R^8$ is amino, methylamino, dimethylamino, diethylamino, azetidinyl, pyrrolidino and morpholino.

Further preferred moieties represented by $ZNR^7R^8$ are those wherein Z is $CH_2$ or $CH_2CH_2$, $R^7$ represents hydrogen, $C_{1-4}$alkyl or $C_{3-6}$cycloalkyl and $R^8$ is $C_{2-4}$alkyl substituted by one or two substituents selected from hydroxy, $C_{1-2}$alkoxy, azetidinyl, pyrrolidino, piperidino, morpholino or thiomorpholino.

In particular, Z is preferably $CH_2$ and $NR^7R^8$ is preferably dimethylamino, azetidinyl or pyrrolidino, especially dimethylamino.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl. A suitable cycloalkylalkyl group may be, for example, cyclopropylmethyl.

As used herein, the terms "alkenyl" and "alkynyl" as a group or part of a group means that the group is straight or branched. Examples of suitable alkenyl groups include vinyl and allyl. A suitable alkynyl group is propargyl.

When used herein the term halogen means fluorine, chlorine, bromine and iodine. The most apt halogens are fluorine and chlorine of which fluorine is preferred.

Specific compounds within the scope of this invention include:

[2S,3S]-1-[(5-(dimethylaminomethyl)-1H-[1,2,3]triazol-4-yl)methyl]-2-phenyl-3-[[5-(1-methyl-1H-1,2,3-triazol-5-yl)benzofuran-7-yl]methyloxy] piperidine;

[2S,3S]-1-[(5-(dimethylaminomethyl)-1H-[1,2,3]triazol-4-yl)methyl]-2-phenyl-3-[(5-(5-methyl-1H-tetrazol-1-yl)benzofuran-7-yl)methyloxy] piperidine;

and pharmaceutically acceptable salts or prodrugs thereof.

Further preferred compounds within the scope of the present invention are described in the Examples described herein.

In a further aspect of the present invention, the compounds of formula (I) will preferably be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

Thus, for example, certain preferred prodrugs may not be antagonists of tachykinin, particularly substance P, activity to any significant extent (or not at all). Such compounds, however, are still advantageous in treating the various conditions described herein, especially where an injectable formulation is preferred.

The advantages of a prodrug may lie in its physical properties, such as enhanced water solubility for parenteral administration compared with the parent drug, or it may enhance absorption from the digestive tract, or it may enhance drug stability for long-term storage. Ideally a prodrug will improve the overall efficacy of a parent drug, for example, through the reduction of toxicity and unwanted effects of drugs by controlling their absorption, blood levels, metabolism, distribution and cellular uptake.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I), (Ia), (Ib) and (Ic), will have the 2- and 3-substituent cis. The preferred stereochemistry at the 2-position is either (R) when A is —O— or (S) when A is —$CH_2$—, for instance, that possessed by the compound of Example 1 (i.e. 2-(S)). The preferred stereochemistry of the 3-position is that possessed by the compound of Example 1 (i.e. 3-(S)). The preferred stereochemistry of the carbon to which the group Y is either (R) when Y is $C_{1-4}$alkyl (e.g. methyl) or (S) when Y is $C_{1-4}$alkyl substituted by hydroxy (e.g. $CH_2OH$). Thus for example as shown in formula (Id)

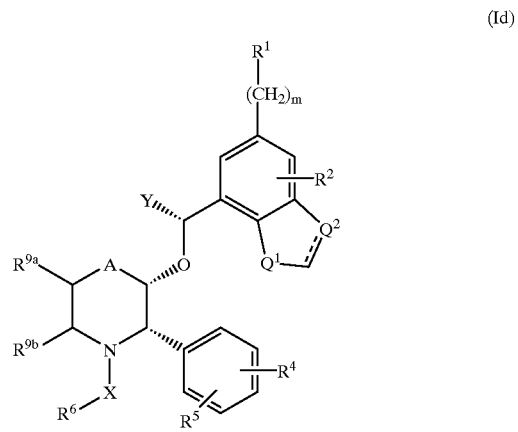

(Id)

The present invention further provides pharmaceutical compositions comprising one or more compounds of formula (I) in association with a pharmaceutically acceptable carrier.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pils and capsules. This solid preformulation composition is then subdivided into unit dosage forms of the type described above containing from 0.1 to about 500 mg of the active ingredient of the present invention. The tablets or pils of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include anionic agents such as sodium bis-(2-ethylhexyl)sulfosuccinate (docusate sodium), cationic agents, such as alkyltrimethylammonium bromides, (e.g. cetyltrimethylammonium bromide (cetrimide)), and in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, lnfonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mising with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention father provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumors, eneuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migrame.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide. Additionally, a compound of formula (I) may be administered in combination with an anti-inflammatory corticosteroid, such as dexamethasone. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.*, (1993) 250, R5-R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and headache, including migraine, acute or chronic tension headache, cluster headache, temporomandibular pain, and maxillary sinus pain.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene D$_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-HT$_1$ agonists, especially sumatriptan.

Likewise, for the treatment of behavioural hyperalgesia, a compound of the present invention may be used in conjunction with an antagonist of N-methyl D-aspartate HNMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of formula (I), a bronchodilator, and a pharmaceutically acceptable carier.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), the compounds according to the invention may be prepared from compounds of formula (II)

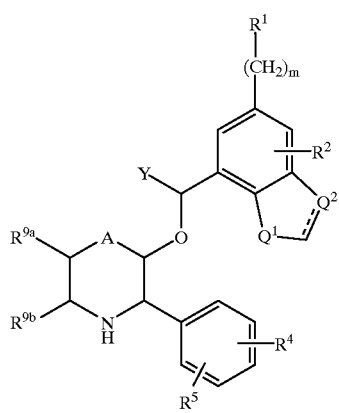

(II)

wherein $R^1$, $R^2$, $R^3$, $R^4$, $R^5$, $R^{9a}$, $R^{9b}$, A, Y, $Q^1$, $Q^2$, the dotted line and m are as defined in relation to formula (I) by reaction with a compound of formula (III):

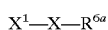

(III)

where X is as defined in relation to formula (I), $R^{6a}$ is a group of the formula $R^6$ as defined in relation to formula (I) or a precursor therefor and $X^1$ is a leaving group such as bromine or chlorine; and, if $R^{6a}$ is a precursor group, converting it to a group $R^6$ (in which process any reactive group may be protected and thereafter deprotected if desired).

This reaction may be performed in conventional manner, for example in an organic solvent such as dimethylformamide in the presence of an acid acceptor such as potassium carbonate.

According to another process (B), compounds of formula (I) wherein $R^6$ represents 1,2,3-triazol-4-yl substituted by $CH_2NR^7R^8$, and X is —$CH_2$—, may be prepared by reaction of a compound of formula (IV)

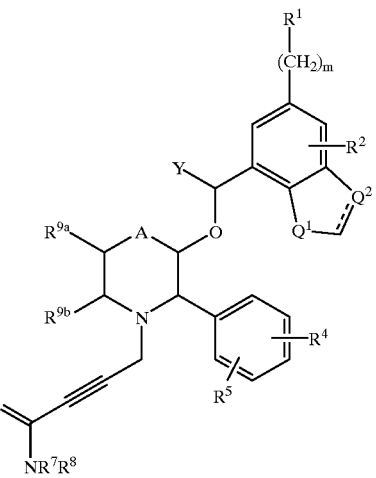

(IV)

with an azide, for example, sodium azide in a suitable solvent such as dimethylsulphoxide at a temperature of between 40° C. and 100° C., followed by reduction of the carbonyl group adjacent to —$NR^7R^8$ using a suitable reducing agent such as lithium aluminum hydride at at a temperature between −10° C. and room temperature, conveniently at room temperature.

Alternatively, according to a process (C), compounds of formula (I) wherein $R^6$ represents 1,2,3-triazol-4-yl substituted by CH2$NR^7R^8$, and X is —$CH_2$—, may be prepared by reaction of a compound of formula (V)

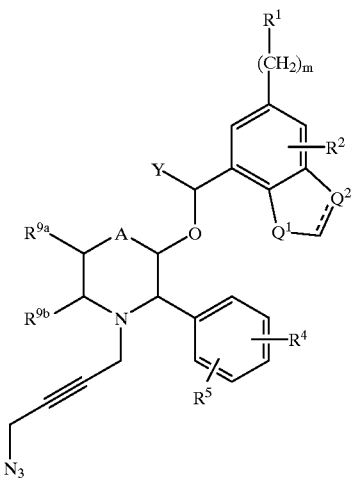

(V)

with an amine of formula $NHR^7R^8$, in a suitable solvent such as an ether, for example, dioxan, at elevated temperature, for example, between 50° C. and 100° C., in a sealed tube, or the like. This reaction is based upon that described in *Chemische Berichte* (1989) 122, p. 1963.

According to another process, (D), compounds of formula (I) wherein $R^6$ represents substituted or unsubstituted 1,3,5-triazine may be prepared by reaction of intermediates of formula (VI):

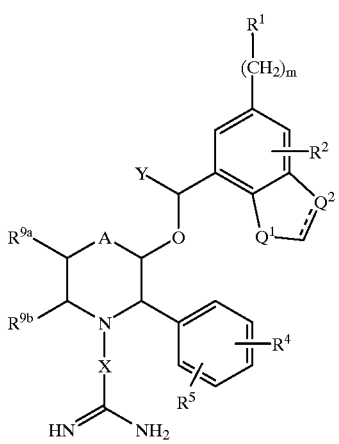

(VI)

with substituted or unsubstituted 1,3,5-triazine.

The reaction is conveniently effected in a suitable organic solvent, such as acetonitrile, at elevated temperature, such as 80–90° C., preferably about 82° C.

According to a further process, (E), compounds of formula (I) wherein $R^6$ represents substituted or unsubstituted 1,2,4-triazine may be prepared by reaction of an intermediate of formula (VII) with a dicarbonyl compound of formula (VIII):

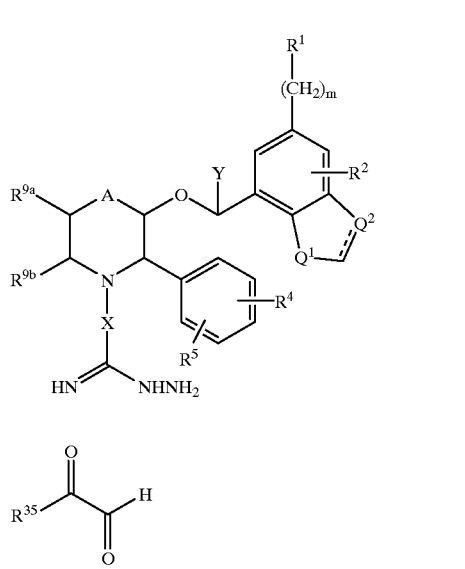

(VII)

(VIII)

wherein $R^{35}$ represents H or a suitable substituent such as $ZNR^7R^8$.

The reaction is conveniently effected in a suitable organic solvent, such as an ether, e.g. tetrahydrofuran, conveniently at ambient temperature.

According to a further process (F), compounds of formula (I) wherein $R^6$ represents a substituted 1,2,4-triazolyl group may be prepared by reaction of an intermediate of formula (II) with a compound of formula (IX)

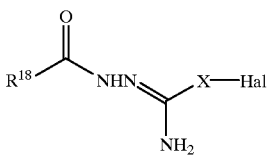

(IX)

wherein X is as defined in relation to formula (I), Hal is a halogen atom, for example, bromine, chlorine or iodine and $R^{18}$ is H, $CONH_2$ or $OCH_3$ (which is converted to an oxo substituent under the reaction conditions), in the presence of a base, followed where necessary by conversion to a compound of formula (I), for example, by reduction of the $CONH_2$ group to $CH_2NH_2$.

Suitable bases of use in the reaction include alkali metal carbonates such as, for example, potassium carbonate. The reaction is conveniently effected in an anhydrous organic solvent such as, for example, anhydrous dimethylformamide, preferably at elevated temperature, such as about 140° C.

A suitable reducing agent for the group $CONH_2$ is lithium aluminium hydride, used at between −10° C. and room temperature.

According to another process, (G), compounds of formula (I) wherein $R^6$ represents thioxotriazolyl may be prepared from intermediates of formula (X)

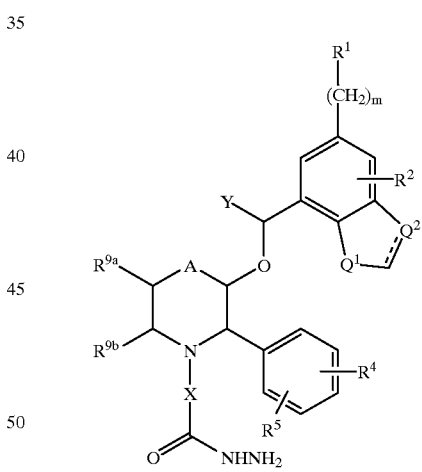

(X)

by reaction with a compound of formula HNCS, in the presence of a base.

Suitable bases of use in the reaction include organic bases such as, for example, 1,8-diazabicyclo[5.4.0]undec-7-ene DBU). The reaction is conveniently effected in a suitable organic solvent, such as alcohol, e.g. butanol.

According to a further alternative general process (H), compounds of formula (I) wherein the heterocycle $R^6$ is substituted by $ZNR^7R^8$, may be prepared from an intermediate of formula (II) as defined above with one of the compounds of formula (XI):

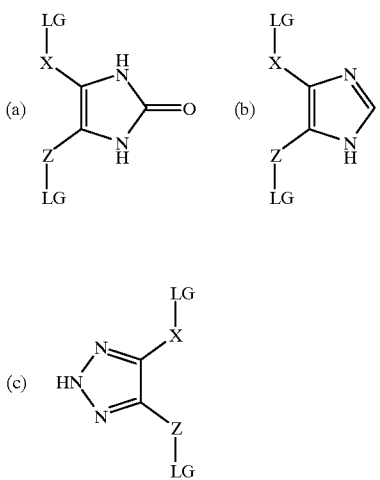

(XI)

(a), (b), (c)

wherein each LG, which may be the same or different, is a leaving group, such as an alkyl- or arylsulphonyloxy group (e.g. mesylate or tosylate) or, in particular, a halogen atom, (e.g. bromine, chlorine or iodine) and X and Z are as defined in formula (I), followed by reaction of the resultant compound with an amine NHR$^7$R$^8$ to complete the ZNR$^7$R$^8$ moiety.

This reaction is conveniently effected in an organic solvent such as dimethylformamide in the presence of an acid acceptor such as potassium carbonate.

It will be appreciated that, where necessary, reactive groups may be protected, thus for example, the NH groups of an imidazolinone of formula (XIa) may be protected by any suitable amine protecting group such as an acetyl group.

According to another general process (J), compounds of formula (I) may be prepared by reaction of intermediates of formula (XII)

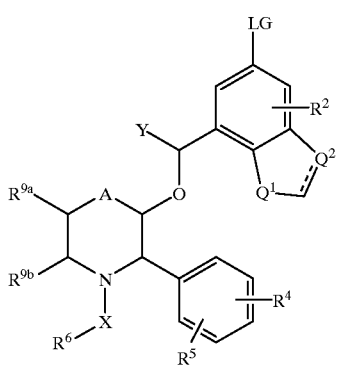

(XII)

wherein LG is a suitable leaving group such as a halogen atom, e.g. bromine or iodine, or —OSO$_2$CF$_3$, with a compound of formula (XIII)

R$^1$—(CH$_2$)$_m$—R$^{40}$ (XIII)

wherein R$^{40}$ is B(OH)$_2$, Sn(alkyl)$_3$, for example, Sn(methyl)$_3$ or Sn(n-butyl)$_3$. Where R$^{40}$ is B(OH)$_2$, the reaction is conveniently effected in the presence of a palladium (0) catalyst such as tetrakis(triphenylphosphine) palladium (0), in a siutable solvent such as an ether, for example, dimethoxyethane, at an elevated temperature. Where R$^{40}$ is Sn(alkyl)$_3$, the reaction is conveniently effected in the presnce of a palladium (II) catalyst such as bis(triphenylphosphine) palladium (II) chloride, in a suitable solvent such as an aromatic hydrocarbon, for example, toluene, at an elevated temperature.

According to a preferred process (K) compounds of formula (I) wherein R$^1$ is a tetrazol-1-yl group and m is zero, may be prepared by the reaction of intermediates of formula (XIV)

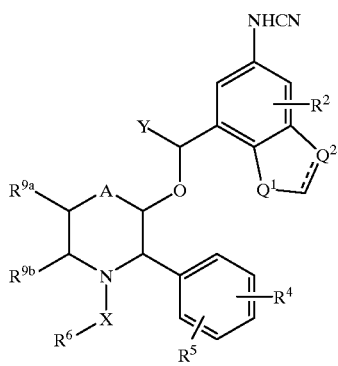

(XIV)

with ammonium chloride and sodium azide at elevated temperature, conveniently in a solvent such as dimethylformamide.

Further details of suitable procedures will be found in the accompanying Examples.

Compounds of formula (I) may also be prepared from other compounds of formula (I) using suitable interconversion procedures. For example, compounds of formula (I) wherein X represents C$_{1-4}$alkyl may be prepared from compounds of formula (I) wherein X represents C$_{1-4}$alkyl substituted by oxo by reduction, for example, using borane or lithium aluininium hydride. Suitable interconversion procedures will be readily apparent to those skilled in the art.

Intermediates of formula (IV) may be prepared from intermediates of formula (II) by reaction with an acetylene compound of formula HC≡C—CH$_2$—Hal in the presence of a base such as potassium carbonate in a suitable solvent such as dimethylformamide, conveniently at room temperature, followed by reaction of the resultant acetylene intermediate with an amide of formula Hal—CO—NR$^7$R$^8$ in the presence of suitable catalysts including bis (triphenylphosphine) palladium(II) chloride, copper(I) iodide and triphenylphosphine in a suitable solvent such as triethylamine, preferably at reflux.

Intermediates of formula (V) may be prepared from a compound of formula (XV)

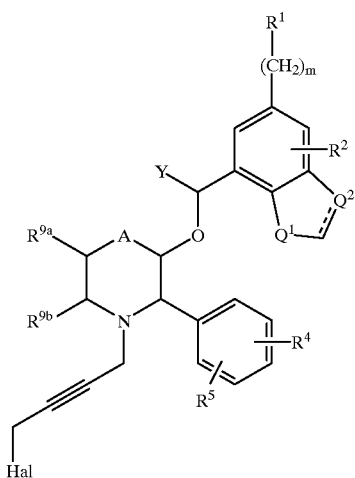

(XV)

wherein Hal is a halogen atom, for example, chlorine, bromine or iodine, especially chlorine, by reaction with an azide, for example, sodium azide in a suitable solvent such as dimethylsulphoxide at or below room temperature.

Compounds of formula (XV) may be prepared by a dropwise addition of an intermediate of formula (II) to a dihaloacetylene of formula Hal—CH$_2$—C≡C—CH$_2$—Hal where each Hal is independently chlorine, bromine or iodine, especially chlorine. The reaction is conveniently effected in a suitable solvent such as dimethylformamide in the presence of a base such as potassium carbonate.

Intermediates of formula (VI) may be prepared from intermediates of formula (II) by reaction with a compound of formula Hal—X—C(NH)NH$_2$, where Hal and X are as previously defined.

Intermediates of formula (VID) may be prepared from intermediates of formula (II) by reaction with a compound of formula Hal—X—C(NH)NHNH—Boc, wherein Hal and X are as previously defined and Boc stands for t-butoxycarbonyl, followed by deprotection under acidic conditions.

Compounds of formula (VIII) are commercially available or may be prepared from commercially available compounds by known methods.

Compounds of formula (IX) may be prepared as described in *J. Med. Chem.*, (1984) 27, 849.

Intermediates of formula (X) may be prepared from the corresponding ester by treatment with hydrazine. The reaction is conveniently effected in a suitable organic solvent, such as an alcohol, for example, ethanol, at elevated temperature.

For compounds wherein R$^6$ is a heterocycle substituted by a ZNR$^7$R$^8$ group where Z is CH$_2$, certain favored compounds of formula (I) may be prepared from a corresponding compound with a hydrogen atom in place of the ZNR$^7$R$^8$. Thus, for example a compound of the formula (I) wherein R$^6$ is an imidazolinone group carrying a CH$_2$NR$^7$R$^8$ moiety may be prepared from a corresponding compound lacking the CH$_2$NR$^7$R$^8$ moiety by reaction with formaldehyde and an amine NHR$^7$R$^8$ under conventional Mannich reaction conditions, for example in methanol with heating. If desired a pre-formed reagent such as R$^7$R$^8$N$^+$=CH$_2$.I$^-$ may be employed and a tertiary amine such as triethylamine used as acid acceptor.

Alternatively a compound of formula (I) wherein R$^6$ is an imidazolinone group lacking a CH$_2$NR$^7$R$^8$ may be reacted with paraformaldehyde and an amine for example a secondary amine such as pyrrolidine to give a compound wherein the imidazolinone ring is substituted by CH$_2$NR$^7$R$^8$ where R$^7$, R$^8$ and the nitrogen atom to which they are attached form a heteroaliphatic ring of 4 to 7 ring atoms which may optionally contain an oxygen ring atom or a second nitrogen atom which will be part of a NH or NR$^c$ moiety, where R$^c$ is as previously defined.

This reaction may be performed in a conventional manner, for instance, in a suitable solvent such as an alcohol, for example, methanol at an elevated temperature up to the boiling point of the solvent.

Compounds of formulae (XII and (XIV) may be prepared by reacting a compound of formula (XVI) or (XVII)

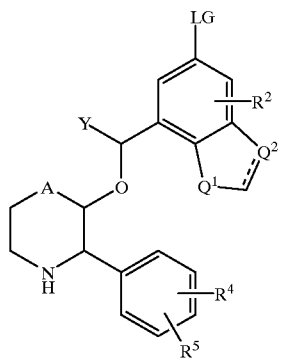

(XVI)

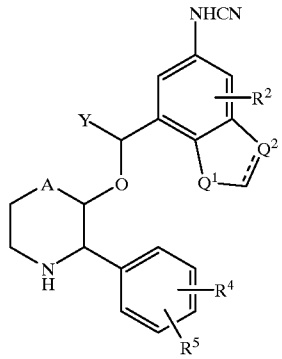

(XVII)

respectively, with any suitable reagent for completing the R$^6$—X— moiety as described in any one of processes (A) to (H).

Alternatively, compounds of formula (XII) may be preapred by reacting a compound of formula (XVIII)

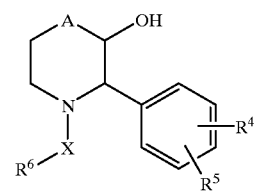

(XVIII)

with a compound of formula (XIX)

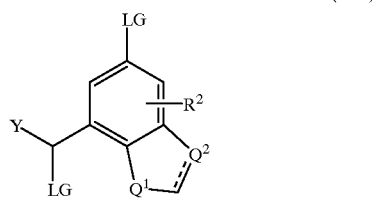

where each LG independently represents a leaving group as previously defined.

Compounds of formula (XIII) and (XIX) may be prepared by conventional methodology, such as that described in International patent specification No. WO 95/06645, published Mar. 9, 1995.

In an alternative two-step method, the hydroxy compound of formula (I) may be reacted with a suitable base such as sodium hydride in tetrahydrofuran, and tetrabenzylpyrophosphate added to yield the dibenzyl-protected phosphate which may be deprotected as described above.

The compounds of the formula (II), wherein A is —$CH_2$—, may be prepared by methods known in the art, for example as described in European patent specification No. 0 528 495-A, published Feb. 24, 1993.

The compounds of the formula (II), wherein A is —O—, may be prepared as shown in the following Scheme in which $Ar^1$ represents the $R^1$, $R^2$, $R^3$ substituted phenyl group; $Ar^2$ represents the $R^4$, $R^5$ substituted phenyl group and Ph represents phenyl:

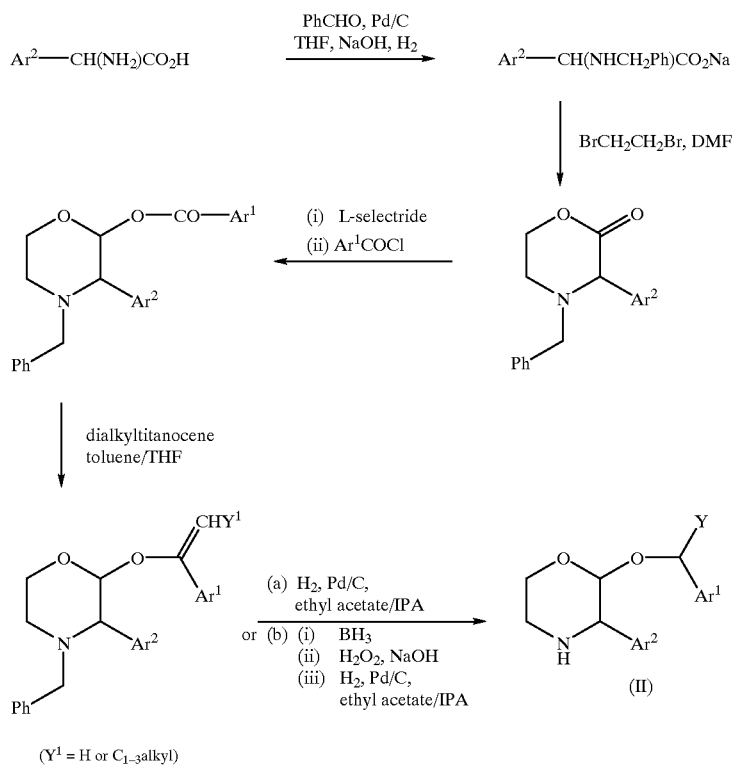

($Y^1$ = H or $C_{1-3}$alkyl)

The preferred phosphate prodrugs of the compounds of the present invention are those wherein Y is a derivatized hydroxy substituted $C_{1-4}$alkyl group. Such preferred compounds may be prepared in a stepwise manner from a compound of formula (I) wherein Y is, for example, —$CH_2OH$—.

Thus, the hydroxy compound is first treated with dibenzyloxydiethylaminophosphine in a suitable solvent such as tetrahydrofuran, preferably in the presence of an acid catalyst such as tetrazole. The resultant compound (Y=$CH_2OP(OCH_2Ph)_2$) is then oxidised using, for example, 4-methylmorpholine-N-oxide to give the dibenzyl-protected phosphate. Deprotection by catalytic hydrogenation or transfer hydrogenation (palladium catalyst on carbon and ammonium formate), in a suitable solvent such as methanol at reflux, yields the desired phosphate prodrug which may be converted to any desired salt form by conventional methodology.

L-Selectride is lithium tri-sec-butylborohydride.

The following references describe methods which may be applied by the skilled worker to the chemical synthesis set forth above once the skilled worker has read the disclosure herein:

(i) D. A. Evans et al., *J. Am. Chem. Soc.*, (1990) 112, 4011.

(ii) I. Yanagisawa et al., *J. Med. Chem.*, (1984) 27, 849.

(iii) R. Duschinsky et al., *J. Am. Chem. Soc.*, (1948) 70, 657.

(iv) F. N. Tebbe et al., *J. Am. Chem. Soc.*, (1978) 100, 3611.

(v) N. A. Petasis et al., *J. Am. Chem. Soc.*, (1990) 112, 6532.

(vi) K. Takai et al., *J. Org. Chem.*, (1987) 52, 4412.

The Examples disclosed herein produce predominently the preferred isomers. The unfavored isomers are also produced as minor components. If desired they may be isolated and employed to prepare the various stereoisomers in conventional manner, for example chromatography using an appropriate column. However, the skilled worker will appreciate that although the Examples have been optimized to the production of the preferred isomers, variation in solvent, reagents, chromatography etc can be readily employed to yield the other isomers.

It will be appreciated that compounds of the formula (I) wherein $R^6$ contains an =O or =S substituent can exist in tautomeric forms. All such tautomeric forms and mixtures thereof are included within this invention. Most aptly the =O or =S substituent in $R^6$ is the =O substituent.

Where they are not commercially available, the intermediates of formula (III) above may be prepared by the procedures described in the accompanying Examples or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds or, in the case of prodrugs, the parent compounds, were found to be active with $IC_{50}$ at the $NK_1$ receptor of less than 100 nM on said test method.

The following non-limiting Examples further illustrate the present invention:

DESCRIPTION 1

[2S,3S]-1-tert-Butoxycarbonyl-2-phenyl-3-[(5-bromobenzofuran-7-yl)methyloxy]piperidine (i) 4-Bromo-1-[(2,2-dimethoxyethyl)oxy]-2-methylbenzene Bromoacetaldehyde dimethylacetal (6.05 ml) was added to a stirred solution of 4-bromo-2-methylphenol (10.0 g) and KOH (5.0 g) in dry DMSO (40 ml). The solution was warmed to 100° C. for 4 hours. After this time the reaction mixture was cooled to room temperature and poured into water (200 ml). The aqueous layer was extracted with ether (2×100 ml). The combined organic layers were separated, washed with 2N aqueous NaOH (2×50 ml), dried over $MgSO_4$, filtered, and the solvent removed under reduced pressure to afford a brown oil. Purification by MPLC (15% ethyl acetate/n-hexane) afforded 4-bromo-1-[(2,2-dimethoxyethyl)oxy]-2-methylbenzene as a colourless oil (6.24 g). $^1H$ NMR (360 MHz,CDCl$_3$)δ2.21 (3H, s), 3.46 (6H,s), 3.98 (2H, d, J=3.6 Hz), 4.69 (1H, t, J=3.6 Hz), 6.56 (1H, d, J=7.2 Hz), 7.26 (1H, d, J=7.2 Hz), 7.39 (1H, s).

(ii) 5-Bromo-7-methyl-benzofuran

Polyphosphoric acid (2.0 g) was added to a solution of 4-bromo-1-[(2,2-dimethyloxyethyl)oxy]-2-methylbenzene (6.24 g) in toluene (100 ml) and the resulting mixture was warmed to reflux for 4 hours. The reaction mixture was cooled to room temperature and the supernatant organic layer decanted off. The black residue was basified with 2N aqueous $Na_2CO_3$ and extracted with ethyl acetate (100 ml). The organic layers were combined, washed with brine (2×100 ml), dried over $MgSO_4$, ifitered, and the solvent removed under reduced pressure. Purification by MPLC (2% ethyl acetatein-hexane) gave 5-bromo-7-methyl-benzofaran as a colourless oil (2.77 g). $^1H$ NMR (360 MHz,CDCl$_3$) δ2.48 (3H, s), 6.68 (1H, d, J=3.6 Hz), 7.13 (1H, s), 7.53 (1H, s), 7.60 (1H, d, J=3.6 Hz).

iii) 5-Bromo-7-bromomethyl Benzofuran

N-Bromosuccinimide (10.0 g) and di-benzoylperoxide (500 mg) were added in five equal portions to a solution of 5-bromo-7-methylbenzofuran (9.7 g) stirring at reflux in $CCl_4$ (100 ml), whilst being irradiated with an 850 W lamp. After the final addition, the reaction was stirred at reflux for a further 2 hours, then cooled to room temperature. The solution was filtered and the filtrate washed with 2N NaOH—$H_2O$ (40 ml), brine (40 ml), dried over $MgSO_4$, filtered and the solvent removed under reduced pressure. Purification by MPLC (1% ethyl acetateln-hexane) gave 5-bromo-7-bromomethyl benzofuran as a dlear oil (4.2 g). $^1H$ NMR (360 MHz,CDCl$_3$)δ4.86 (2H, s), 6.69 (1H, d, J=3.0 Hz), 7.54 (1H, s), 7.62 (1H, s), 7.86 (1H, d, J=3.0 Hz).

(iv) [2S,3S]-1-tert-Butoxycarbonyl-2-phenyl-3-[(5-bromobenzofuran-7-yl)methyloxy]piperidine Potassium bis(trimethylsilyl)amide (300 mg) was added to a stirred solution of [2S,3S]-N-tert-butoxycarbonyl-2-phenylpiperidine-3-ol (160 mg) in dry 1,2-dimethoxyethane (3.0 ml) under a dry nitrogen atmosphere. After 30 minutes 5-bromo-7-bromomethylbenzofuran (290 mg) was added, and the reaction stirred for 18 hours at room temperature. The resulting mixture was then diluted with water (50 ml), and extracted into ethyl acetate (2×50 ml). The organic layers were separated and washed with brine (20 ml), dried over $MgSO_4$, filtered and the solvent removed under reduced pressure. Purification by MPLC (20% ethyl acetate/n-hexane), afforded [2S,3S]-1-tert-butoxycarbonyl-2-phenyl-3-[(5-bromobenzofuran-7-yl)methyloxy]piperidine as a yellow gum (136 mg). $^1H$ NMR (360 MHz,CDCl$_3$) δ1.43 (9H, s), 1.65 (2H, m), 1.92 (2H, m), 2.70 (1H, t d, J=7.2, 3.0 Hz), 3.74 (2H,m), 4.90 (2H, d, J=5.0 Hz), 5.74 (1H, br s), 6.71 (1H, d, J=1.0 Hz), 7.30–7.42 (4H, m), 7.58 (3H, m), 7.75 (1H, d, J=1.0 Hz); MS m/z CI$^+$487 (M+H$^+$).

DESCRIPTION 2

1-Methyl-5-tributylstannanyl-1H-[1,2,3]triazole

A solution of 1-methyl-1H-[1,2,3]triazole (350 mg) in dry tetrahydrofuran (5.0 ml) was added dropwise under nitrogen to a stirred, cooled (−78° C.) solution of n-butyl lithium (2.81 ml of 1.6M solution in hexanes) in dry tetrahydrofuran (10 ml). After 1 hour tributylchlorostannane (1.46 g) was added. The reaction was maintained at −78° C. for 30 min. and then allowed to warm to room temperature over 2 hours. The reaction mixture was diluted with brine (10 ml) and extracted into ethyl acetate (50 ml). The organic layer was separated, washed with brine (50 ml), dried over $MgSO_4$, filtered and the solvent removed under reduced pressure. The residue was purified by flash column chromatography (20% ethyl acetate/n-hexane), to give 1-methyl-5-tributylstannanyl-1H-[1,2,3]triazole as a yellow oil (1.03 g). $^1H$ NMR (360 MHz,CDCl$_3$)δ0.87 (9H, m), 1.15 (6H, m), 1.28 (6H, m), 1.36 (6H, m), 4.02 (3H, s), 7.60 (1H, s); MS m/z CI$^+$372 (M+H$^+$).

DESCRIPTION 3

[2S,3S]-2-Phenyl-3-{[5-(1-methyl-1H-[1,2,3]triazol-5-yl)benzofuran-7-yl]methyloxy}piperidine hydrochloride (i) [2S,3S]-1-tert-Butoxycarbonyl-2-phenyl-3{[5-(1-methyl-1H-[1,2,3]triazol-5-yl)benzofuran-7-yl]-methyloxy}piperidine Bis(triphenylphosphine)palladium dichloride (5.0 mg) was added to a degassed solution of [2S,3S]-1-tert-butoxycarbonyl-2-phenyl-3-[(5-bromobenzofuran-7-yl) methyloxy]piperidine (111 mg), and 1-methyl-5-tributylstannanyl-1H-[1,2,3]triazole (165 mg) in dry toluene (5.0 ml) under a dry nitrogen atmosphere. The resulting solution was warmed to reflux for 18 hours. After this time the reaction was cooled to room temperature and the solvent removed under reduced pressure. The residue was partitioned between aqueous NaHCO$_3$ solution (10 ml, sat) and ethyl acetate. The organic layer was washed with brine (10 ml), dried over MgSO$_4$, filtered and the solvent removed under pressure. Purification by MPLC (1:1 ethyl acetate/n-hexane) afforded [2S,3S]-1-tert-butoxycarbonyl-2-phenyl-3-{[5-(1-methyl-1H-[1,2,3]triazol-5-yl)benzofuran-7-yl] methyloxy}piperidine as a yellow foam (51 mg). $^1$H NMR (360 MHz,CDCl$_3$)δ1.45 (9H, s), 1.51–1.83 (5H, m), 2.73 (1H, t d, J=7.0, 3.0 Hz), 3.94 (1H, m), 3.96 (3H, s), 5.02 (2H, d, J=1.0 Hz), 5.76 (1H, br s), 6.84 (1H, d, J=1.0 Hz), 7.26 (4H, m), 7.55 (3H, m), 7.70 (2H, br s); MS m/z CI$^+$489 (M+H$^+$).

(ii) [2S,3S]-2-Phenyl-3-{[5-(1-methyl-1H-[1,2,3]triazol-5-yl)benzofuran-7-yl]methyloxy}piperidine hydrochloride A solution of HCl in ethanol (2 ml, 5N) was added to a stirred solution of [2S,3S]-1-tert-butoxyearbonyl-2-phenyl-3-{[5-(1-methyl-1H-[1,2,3]triazol-5-yl)benzofuran-7-yl] methyloxy}piperidine (51 mg) in dry ethanol. After 2 hours the solvent was removed under reduced pressure and the residue was recrystallised from ether/ethanol to afford [2S,3S]-2-phenyl-3-{[5-(1-methyl-1H-[1,2,3]triazol-5-yl) benzofuran-7-yl]methyloxy}piperidine hydrochloride as white needles (12.2 mg), mp 126–127° C. $^1$H NMR (360 MHz, D$_2$O)δ1.65–1.80 (2H, m), 2.20 (1H, m), 2.40 (1H, m), 3.21 (1H, m), 3.63 (1H, m), 3.92 (3H, s), 3.96 (1H, br s), 4.39 (1H, br s), 4.66 (1H, d, J=11.0 Hz), 4.94 (1H, d, J=11.0 Hz), 6.70 (1H, d, J=1.0 Hz), 6.90 (1H, d, J=1.0 Hz), 7.05–7.16 (5H, m), 7.60 (1H, d, J=1.0 Hz), 7.73 (1H, s), 7.78 (1H, d, J=1.0 Hz); MS m/z CI$^+$389 (M+H$^+$).

EXAMPLE 1

[2S,3S]-1-[(5-(Dimethylaminomethyl)-1H-[1,2,3] triazol-4-yl)methlyl -2-phenyl-3-[(5-(1-methyl-1H-[1,2,3]triazol-5-yl)benzofuran-7-yl)methyloxy] piperidine hydrochloride (i) [2S,3S]-1-(4-Chlorobut-2-yn-1-yl)-2-phenyl-3-[(5-(1-methyl-1H-[1,2,3]triazol-5-yl)benzofuran-7-yl)methyloxy] piperidine A solution of [2S,3S]-2-phenyl-3-[(5-(1-methyl-1H-[1,2,3]triazol-5-yl)benzofuran-7-yl)methyloxy]piperidine hydrochloride (230 mg) in N,N-dimethylformamiide (2 ml) was slowly added to a solution of 1,4-dichlorobut-2-yne (106 ml) and potassium carbonate (224 mg) in N,N-dimethylformamide (2.0 ml). The solution was stirred for 18 hours at room temperature and the solvent removed under reduced pressure. To the residue was added water (40 ml) and the product was extracted with ethyl acetate (3×10 ml). The combined organic fractions were washed with water, saturated brine, dried over MgSO$_4$, filtered and the solvent removed under reduced pressure. The residue was purified by MPLC (10% ethyl acetate/hexane) to give [2S,3S]-1-(4-chlorobut-2-yn-1-yl)-2-phenyl-3-[(5-(1-methyl-1H-[1,2,3] triazol-5-yl)benzofuran-7-yl)methyloxy]piperidine as a yellow oil (205 mg). $^1$H NMR (360 MHz,CDCl$_3$) δ1.57 (2H, m), 2.22 (2H, m), 2.98 (1H, m), 3.27 (2H, d, J=3.0 Hz), 3.43 (1H, br s), 3.62 (1H, br s), 3.95 (3H, s), 4.13 (2H, s), 4.46 (1H, d, J=11.0 Hz), 4.82 (2H, d, J=11.0 Hz), 6.77 (1H, d, J=1.0 Hz), 6.87 (1H, s), 7.15 (3H, m), 7.38 (2H, m), 7.43 (1H, s), 7.62 (2H, br s); MS m/z (CI$^+$) 475 (M+H$^+$).

ii) [2S,3S]-1-(4-Azidobut-2-yn-1-yl)-2-phenyl-3-[(5-(1-methyl-1H-[1,2,3]triazol-5-yl)benzofuran-7-yl)methyloxy] piperidine To a solution of [2S,3S]-1-(4-chlorobut-2-yn-1-yl)-2-phenyl-3-[(5-(1-methyl-1H-[1,2,3]triazol-5-yl)benzofuran-7-yl)methyloxy]piperidine (205 mg) in dimethyl sulphoxide (3.0 ml) was added sodium azide (32.5 mg). The solution was stirred for 20 hours at room temperature at which time aqueous ammonium chloride and ethyl acetate were added. The organic phase was separated, washed with water (20 ml), saturated brine (20 ml) dried over MgSO$_4$, filtered and the solvent removed under reduced pressure to give [2S,3S]-1-(4-azidobut-2-yn-1-yl)-2-phenyl-3-[(5-(1-methyl-1H-[1,2,3]triazol-5-yl)benzofaran-7-yl)methyloxy]piperidine as a white solid (120 mg). 1H NMR (360 MHz,CDCl$_3$) δ1.20–1.60 (2H, m), 2.22 (2H, m), 2.67 (1H, m), 2.98 (1H, m), 3.27 (2H, m), 3.47 (1H, br s), 3.62 (1H, br s), 3.91 (2H, s), 3.95 (3H, s), 4.47 (1H, d, J=11.0 Hz), 4.81 (1H, d, J=11.0 Hz), 6.77 (1H, d, J=1.0 Hz), 6.87 (1H, s), 7.15 (3H, m), 7.38 (2H, m), 7.43 (1H, s), 7.62 (2H, br s); MS m/z (CI$^+$) 482 M+H$^+$).

iii) [2S,3S]-1-[(5-(Dimethylaminomethyl)-1H-[1,2,3] triazol-4-yl)methyl]-2-phenyl-3-[(5-(1-methyl-1H-[1,2,3] triazol-5-yl)benzofuran-7-yl)methyloxy]piperidine hydrochloride Dimethylamine (approximately 10 ml) was condensed at −80° C. in a pressure tube and to this was added a solution of (2S,3S]-1-(4-azidobut-2-yn-1-yl)-2-phenyl-3-[(5-(1-methyl-1H-[1,2,3]triazol-5-yl)benzofuran-7-yl)methyloxy] piperidine (120 mg) in dioxan (5 ml). The tube was sealed and the solution was heated at 80° C. for 14 hours. The solvent was evaporated under reduced pressure to dryness and the residue was purified by MPLC [5% methanol in dichloromethane containing 0.25% ammonia (SG. 0.88)] to give [2S,3S]-1-[(5-dimethylaminomethyl)-1H[1,2,3]-triazol-4-yl)methyl]-2-phenyl-3-[(5-(1-methyl-1H-[1,2,3] triazol-5-yl)benzofuran-7-yl)methyloxy]piperidine as a clear oil (47 mg). To a solution of this residue in diethyl ether was added 5M-HCl in ethanol. The solution was evaporated to dryness and the residue recrystallised from ether/ethanol to give [2S,3S]-1-[(5-(Dimethylaminomethyl)-1H-[1,2,3] triazol-4-yl)methyl]-2-phenyl-3-[(5-(1-methyl-1H-[1,2,3] triazol-5-yl)benzofuran-7-yl)methyloxy]piperidine hydrochloride (57 mg) mp 136–138° C. $^1$H NMR (360 MHz,D$_2$O) δ1.64 (1H, m), 1.87 (1H, m), 2.34 (2H, m), 2.65 (6H, s), 3.27 (1H, d, J=14.0 Hz), 3.71–3.78 (3H, m), 3.85 (1H, br s), 3.93 (3H, s), 4.24 (1H, s), 4.33 (1H, d, J=16.0 Hz), 4.38 (1H, d, J=16.0 Hz), 4.69 (1H, d, J=14.0 Hz), 5.00 (1H, d, J=14.0 Hz), 6.79 (1H, s), 6.92 (1H, d, J=1.0 Hz), 7.16 (5H, m), 7.63 (1H, s), 7.74 (1H, s), 7.81 (1H, d, J=1.0 Hz); m/z (CI$^+$) 527 (M+H$^+$).

We claim:
1. A compound of the formula (I):

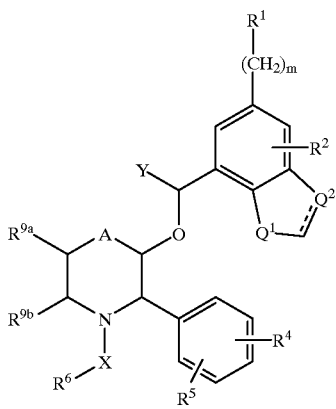

(I)

wherein
R¹ is phenyl or a 5- or 6-membered aromatic heterocyclic group containing 1, 2, 3 or 4 heteroatoms, selected from nitrogen, oxygen and sulphur, which aryl or heteroaryl group is optionally substituted by one or two substituents selected from halogen, $C_{1-6}$alkyl, $C_{1-6}$alkoxy, $CF_3$, $OCF_3$, $NO_2$, CN, $SR^a$, $SOR^a$, $SO_2R^a$, $COR^a$, $CO_2R^a$, $(CH_2)_nCONR^aR^b$, $(CH_2)_nNR^aR^b$ or $(CH_2)_nNR^aCOR^b$, where $R^a$ and $R^b$ are independently hydrogen or $C_{1-4}$alkyl and n is zero, 1 or 2;
R² is hydrogen, halogen, $C_{1-6}$alkyl, $C_{1-6}$alkoxy, $CF_3$, $OCF_3$, $N_2O$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;
R⁴ is hydrogen, halogen, $C_{1-6}$alkyl, $C_{1-6}$alkoxy, $CF_3$, $N_2O$, CN, $SR^a$, $SOR^a$, $SO_2R^a$, $CO_2R^a$, $CONR^aR^b$, $C_{2-6}$akenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;
R⁵ is hydrogen, halogen, $C_{1-6}$alkyl, $C_{1-6}$alkoxy substituted by $C_{1-4}$alkoxy or $CF_3$;
R⁶ is a 5-membered or 6-membered heterocyclic ring containing 2 or 3 nitrogen atoms optionally substituted by =O, =S or a $C_{1-4}$alkyl group, and optionally substituted by a group of the formula $ZNR^7R^8$ where
Z is $C_{1-6}$alkylene or $C_{3-6}$cycloalkylene;
R⁷ is hydrogen, $C_{1-4}$alkyl, $C_{3-7}$cycloalkyl or $C_{3-7}$cycloalkyl$C_{1-4}$alkyl, or $C_{2-4}$alkyl substituted by $C_{1-4}$alkoxy or hydroxyl;
R⁸ is hydrogen, $C_{1-4}$alkyl, $C_{3-7}$cycloalkyl or $C_{3-7}$cycloalkyl$C_{1-4}$alkyl, or $C_{2-4}$alkyl substituted by one or two substituents selected from $C_{1-4}$alkoxy, hydroxyl or a 4, 5 or 6 membered heteroaliphatic ring containing one or two heteroatoms selected from N, O and S;
or R⁷, R⁸ and the nitrogen atom to which they are attached form a heteroaliphatic ring of 4 to 7 ring atoms, optionally substituted by one or two groups selected from hydroxy or $C_{1-4}$alkyl optionally substituted by a $C_{1-4}$alkoxy or hydroxyl group, and optionally containing a double bond, which ring may optionally contain an oxygen or sulphur ring atom, a group S(O) or $S(O)_2$ or a second nitrogen atom which will be part of a NH or $NR^c$ moiety where $R^c$ is $C_{1-4}$alkyl optionally substituted by hydroxy or $C_{1-4}$alkoxy;

or R⁷, R⁸ and the nitrogen atom to which they are attached form a non-aromatic azabicyclic ring system of 6 to 12 ring atoms;
or Z, R⁷ and the nitrogen atom to which they are attached form a heteroaliphatic ring of 4 to 7 ring atoms which may optionally contain an oxygen ring atom;
$R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;
the dotted line is an optional double bond;
A is —$CH_2$—;
Q¹ is oxygen, sulphur or —NH—;
Q² is —N=, —NH—, —CH= or —$CH_2$—;
X is an alkylene chain of 1 to 4 carbon atoms;
Y is hydrogen or a $C_{1-4}$alkyl group optionally substituted by a hydroxyl group; and
m is zero or 1; or a pharmaceutically acceptable salt and prodrug thereof.
2. A compound as claimed in claim 1 of the formula (Ia) or a pharmaceutically acceptable salt or prodrug thereof:

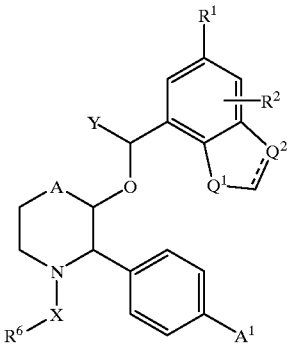

(Ia)

wherein
A, X, Y, R¹, R², R⁶, Q¹, Q² and the dotted line are as defined in claim 1 and A¹ is fluorine or hydrogen.
3. A compound a claimed in claim 1 of the formula (Ib) or a pharmaceutically acceptable salt thereof:

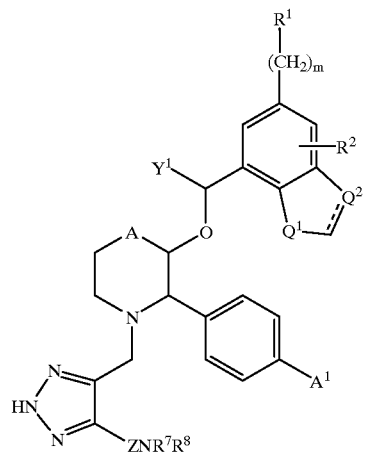

(Ib)

wherein A, Z, R¹, R², R⁷, R⁸, Q¹, Q², the dotted line and m are as defined in claim 1, A¹ is fluorine or hydrogen and Y¹ is hydrogen or methyl.

4. A compound as claimed in of claim 1 of the formula (Ic) or a pharmaceutically acceptable salt thereof:

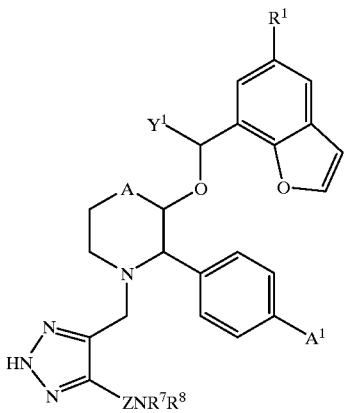

(Ic)

wherein $R^1$, $R^7$, $R^8$ and Z are as defined in claim 3, $A^1$ is fluorine or hydrogen and $Y^1$ is hydrogen or methyl.

5. A compound as claimed in claim 1 of the formula (Id) or a pharmaceutically acceptable salt or prodrug thereof:

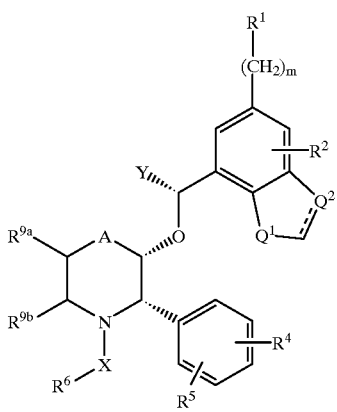

(Id)

wherein A, X, Y, $Q^1$, $Q^2$, $R^1$, $R^2$, $R^4$, $R^5$, $R^6$, $R^{9a}$, $R^{9b}$, m and the dotted line are as defined in claim 1.

6. A compound as claimed in claim 1 wherein X represents $CH_2$, $CH(CH_3)$ or $CH_2CH_2$.

7. A compound as calimed in claim 1 wherein $R^6$ represents a heterocyclic ring selected from:

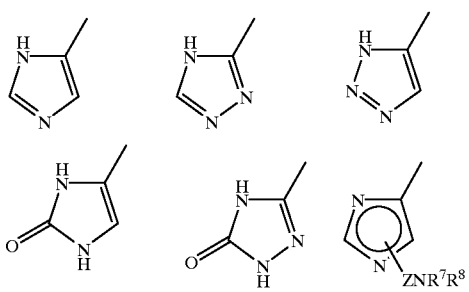

-continued

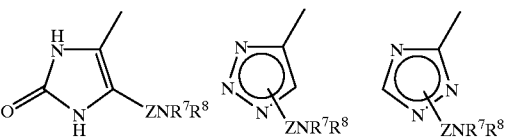

wherein Z, $R^7$ and $R^8$ are as defined in claim 1.

8. A compound as claimed in claim 1 wherein Z is $CH_2$ or $CH_2CH_2$ and $NR^7R^8$ is amino, methylamino, dimethylamino, diethylamino, azetidinyl, pyrrolidino and morpholino.

9. A compound as claimed in claim 1 wherein $R^1$ is the group

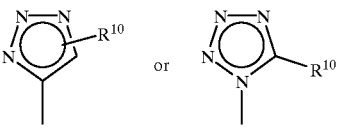

where $R^{10}$ is halogen, $C_{1-6}$alkyl, $C_{1-6}$alkoxy, $CF_3$, $OCF_3$, $N_2O$, CN, $SR^a$, $SOR^a$, $SO_2R^a$, $COR^a$, $CO_2R^a$, $(CH_2)_nCONR^aR^b$, $(CH_2)_nNR^aR^b$ or $(CH_2)_nNR^aCOR^b$, where $R^a$ and $R^b$ are hydrogen or $C_{1-4}$alkyl, and n is zero, 1 or 2.

10. A compound as claimed in claim 1 wherein $Q^1$ is an oxygen atom, $Q^2$ is —CH= or —$CH_2$—, and the dotted line represents a double bond.

11. A compound selected from:

[2S,3S]-1-[(5-(dimethylaminomethyl)-1H-[1,2,3]triazol-4-yl)methyl]-2-phenyl-3-[[5-(1-methyl-1H-1,2,3-triazol-5-yl)benzofuran-7-yl]methyloxy]piperidine;

[2S,3S]-1-[(5-(dimethylaminomethyl)-1H-[1,2,3]triazol-4-yl)methyl]-2-phenyl-3-[(5-(5-methyl-1H-tetrazol-1-yl)benzofuran-7-yl)methyloxy]piperidine;

or a pharmaceutically acceptable salt or prodrug thereof.

12. A pharmaceutical composition comprising a therapeutically effective amount of a compound as claimed in claim 1 in association with a pharmaceutically acceptable carrier or excipient.

13. A method for the treatment or prevention of pain or inflammation which comprises administration to a patient in need thereof of an effective amount of the compound of claim 1.

14. A method for the treatment or prevention of migraine which comprises administration to a patient in need thereof of an effective amount of the compound of claim 1.

15. A method for the treatment or prevention of emesis which comprises administration to a patient in need thereof of an effective amount of the compound of claim 1.

16. A method for the treatment or prevention of postherpetic neuralgia which comprises administration to a patient in need thereof of an effective amount of the compound of claim 1.

17. A process for the preparation of a compound as claimed in claim 1 which comprises:

(A) reaction of a compound of formula (II)

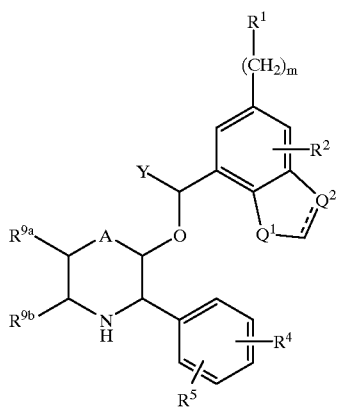

wherein $R^1$, $R^2$, $R^4$, $R^5$, $R^{9a}$, $R^{9b}$, A, Y, $Q^1$, $Q^2$, the dotted line and m are as defined in claim 1, with a compound of formula (III):

$$X^1\text{---}X\text{---}R^{6a} \qquad \text{(III)}$$

where X is as defined in claim 1, $R^{6a}$ is a group of the formula $R^6$ as defined in claim 1 or a precursor therefor and $X^1$ is a leaving group; and, if $R^{6a}$ is a precursor group, converting it to a group $R^6$; or (B), for compounds of formula (I) wherein $R^6$ represents 1,2,3-triazol-4-yl substituted by $CH_2NR^7R^8$, and X is —$CH_2$—, reaction of a compound of formula (IV)

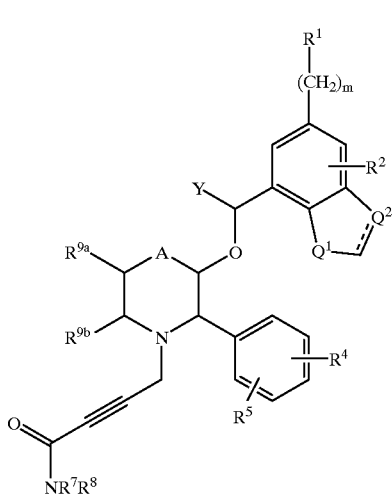

with an azide, followed by reduction of the carbonyl group adjacent to —$NR^7R^8$ using a suitable reducing agent; or (C), for compounds of formula (I) wherein $R^6$ represents 1,2,3-triazol-4-yl substituted by CH2$NR^7R^8$, and X is —$CH_2$—, reaction of a compound of formula (V)

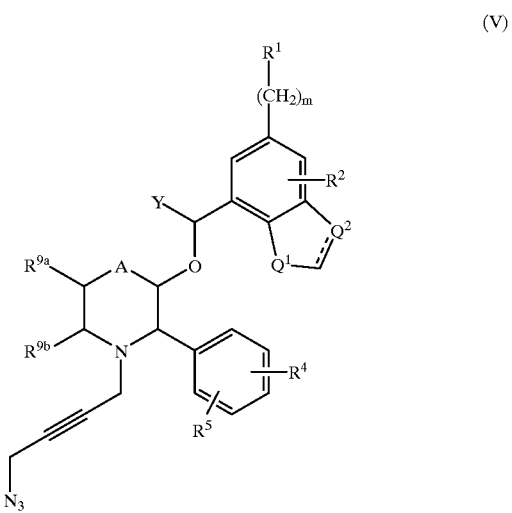

with an amine of formula $NHR^7R^8$; or (D), for compounds of formula (I) wherein $R^6$ represents substituted or unsubstituted 1,3,5-triazine, reaction of intermediates of formula (VI):

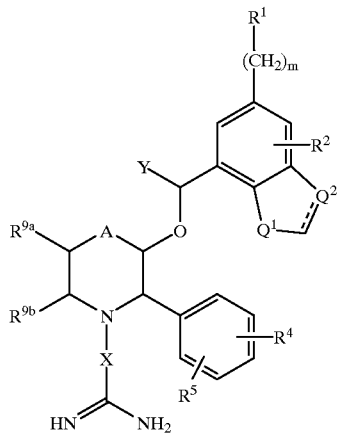

with substituted or unsubstituted 1,3,5-triazine; or (E), for compounds of formula (I) wherein $R^6$ represents substituted or unsubstituted 1,2,4-triazine, reaction of an intermediate of formula (VII) with a dicarbonyl compound of formula (VIII):

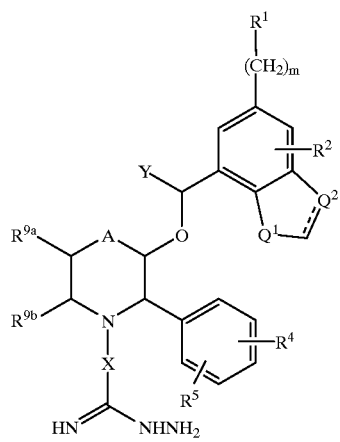

(VII)

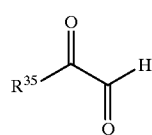

(VIII)

wherein $R^{35}$ represents H or a suitable substituent such as $ZNR^7R^8$; or (F), for compounds of formula (I) wherein $R^6$ represents a substituted 1,2,4-triazolyl group, reaction of an intermediate of formula (II) with a compound of formula (IX)

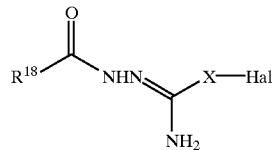

(IX)

wherein X is as defined in claim 1, Hal is a halogen atom, and $R^{18}$ is H, $CONH_2$ or $OCH_3$ (which is converted to an oxo substituent under the reaction conditions), in the presence of a base, followed where necessary by conversion to a compound of formula (I); or (G), for compounds of formula (I) wherein $R^6$ represents thioxotriazolyl, reaction of an intermediate of formula (X)

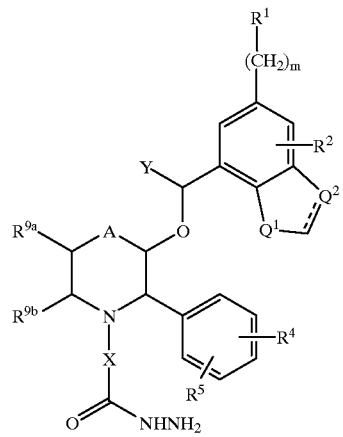

(X)

with a compound of formula HNCS, in the presence of a base; or (H), for compounds of formula (I) wherein the heterocycle $R^6$ is substituted by $ZNR^7R^8$, reaction of an intermediate of formula (II) as defined above with one of the compounds of formula (XI):

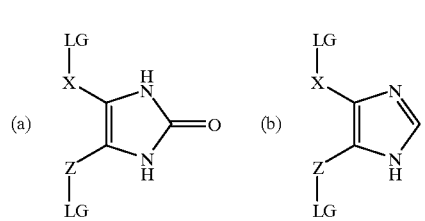

(XI)

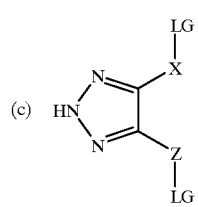

wherein each LG, which may be the same or different, is a leaving group, and X and Z are as defined in claim 1, followed by reaction of the resultant compound with an amine $NHR^7R^8$ to complete the $ZNR^7R^8$ moiety; or (J), reaction of intermediates of formula (XII)

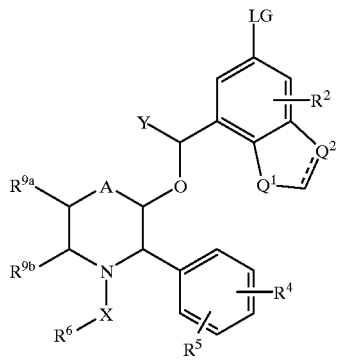
(XII)

wherein LG is a leaving group, with a compound of formula (XIII)

$$R^1—(CH_2)_m—R^{40} \qquad \text{(XIII)}$$

wherein $R^{40}$ is $B(OH)_2$ or $Sn(alkyl)_3$, in the presence of a palladium catalyst; or (K), for compounds of formula (I) wherein $R^1$ is a tetrazol-1-yl group and m is zero, reaction of intermediates of formula (XIV)

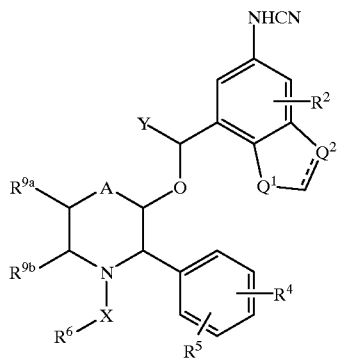
(XIV)

with ammonium chloride and sodium azide at elevated temperature;

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt or prodrug thereof.

* * * * *